US011160948B2

(12) United States Patent
Mansi

(10) Patent No.: US 11,160,948 B2
(45) Date of Patent: Nov. 2, 2021

(54) NEBULIZER TUBING WITH A PORT TO MINIMIZE MEDICAMENT LOSS

(71) Applicant: Imam Abdulrahman Bin Faisal University, Dammam (SA)

(72) Inventor: Ahmed Abdelkarim Mansi, Al Khobar (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 217 days.

(21) Appl. No.: 15/189,706

(22) Filed: Jun. 22, 2016

(65) Prior Publication Data

US 2017/0368295 A1 Dec. 28, 2017

(51) Int. Cl.

| | |
|---|---|
| ***A61M 16/20*** | (2006.01) |
| ***A61M 16/08*** | (2006.01) |
| ***A61M 11/02*** | (2006.01) |
| ***A61M 16/06*** | (2006.01) |

(52) U.S. Cl.

CPC .......... *A61M 16/201* (2014.02); *A61M 11/02* (2013.01); *A61M 16/0683* (2013.01); *A61M 16/0816* (2013.01); *A61M 16/0875* (2013.01); *A61M 16/06* (2013.01)

(58) Field of Classification Search

CPC ........................... A61M 11/005; A61M 11/02; A61M 15/0015; A61M 15/0018; A61M 15/0016; A61M 15/0091; A61M 15/0093; A61M 16/20; A61M 16/0093; A61M 16/201; A61M 16/0683; A61M 16/0816; A61M 16/0875; A61M 16/06; A61M 16/208; A61M 16/206; A61M 16/08; A61M 2016/0015; A61M 2016/003; A61M 1/0047; A61F 2005/4415; F16K 24/04

See application file for complete search history.

(56) References Cited

U.S. PATENT DOCUMENTS

| | | | | | |
|---|---|---|---|---|---|
| 3,197,172 | A * | 7/1965 | Brandenberg | F16K 24/04 | 222/477 |
| 3,385,559 | A * | 5/1968 | Churchill | F16B 1/00 | 251/70 |
| 3,625,221 | A * | 12/1971 | Corbett | A61M 1/0047 | 251/145 |
| 4,098,290 | A * | 7/1978 | Glenn | A61M 16/12 | 128/204.25 |
| 4,462,397 | A * | 7/1984 | Suzuki | A61M 16/08 | 128/200.14 |
| 4,502,481 | A * | 3/1985 | Christian | A61M 16/00 | 128/205.24 |

(Continued)

FOREIGN PATENT DOCUMENTS

CN 203989325 U 12/2014

*Primary Examiner* — Jan Christopher L Merene
*Assistant Examiner* — Brian T Khong
(74) *Attorney, Agent, or Firm* — Oblon, McClelland, Maier & Neustadt, L.L.P.

(57) ABSTRACT

A nebulizer tubing including an inlet configured to be connected to a gas source and an outlet configured to be connected to a nebulizer. The nebulizer tubing includes a port configured to be covered during inhalation to allow airflow from the gas source to the nebulizer and uncovered during exhalation to stop the airflow from the gas source to the nebulizer by allowing gas to escape from the nebulizer tubing. The airflow activates a nebulization process.

4 Claims, 8 Drawing Sheets

(56) References Cited

U.S. PATENT DOCUMENTS 4,657,007 A * 4/1987 Carlin .................... A61M 11/06 128/200.18
5,040,532 A * 8/1991 Alfery ................... A61M 16/08 128/205.11
5,372,594 A * 12/1994 Colacello ................ A61F 5/441 55/385.4
5,458,138 A * 10/1995 Gajo ................... A61M 1/0001 128/205.12
5,603,315 A * 2/1997 Sasso, Jr. .......... A61M 16/0677 128/204.18
5,666,945 A * 9/1997 Davenport ............ A61M 16/20 128/200.14
6,076,523 A * 6/2000 Jones .................... A61M 16/12 128/204.21
6,152,886 A * 11/2000 Phelan ................ A61M 1/0047 433/91
6,412,481 B1 * 7/2002 Bienvenu .......... A61M 15/0086 128/200.21
6,422,237 B1 * 7/2002 Engel ..................... A61H 31/00 128/204.18
6,460,537 B1 10/2002 Bryant et al.
6,659,100 B2 * 12/2003 O'Rourke ......... A61M 15/0086 128/200.21
6,772,754 B1 * 8/2004 Mendenhall ...... A61M 15/0091 128/200.14
7,204,245 B2 * 4/2007 Johnson ............ A61M 15/0086 128/200.14
8,245,705 B2 8/2012 Li
8,973,572 B2 3/2015 Chen et al.
9,566,399 B1 * 2/2017 Bono ................... A61M 11/003
2002/0046753 A1 * 4/2002 Lamb .................... A61M 16/12 128/204.25
2004/0159323 A1 * 8/2004 Schmidt .............. A61M 16/026 128/204.23
2005/0004520 A1 * 1/2005 Lemoine .............. A61C 17/043 604/118
2005/0217666 A1 * 10/2005 Fink ................... A61K 31/7036 128/200.14
2006/0021613 A1 2/2006 Overlander
2007/0049841 A1 * 3/2007 Lepel ..................... A61M 11/02 600/534
2007/0101994 A1 * 5/2007 Waters ................... A61M 11/06 128/205.12
2008/0000472 A1 * 1/2008 Wall ...................... A61M 16/20 128/202.27
2008/0168988 A1 * 7/2008 Lu .......................... A61M 11/06 128/203.15
2010/0043790 A1 * 2/2010 Tatarek .................. A61M 11/06 128/203.14
2010/0180891 A1 * 7/2010 McKinnon ............. A61M 11/06 128/203.12
2011/0253134 A1 10/2011 Chen et al.
2013/0327323 A1 * 12/2013 Rubin .................... A61M 11/02 128/200.18
2014/0238398 A1 * 8/2014 Christopher ...... A61M 16/0816 128/204.22
2015/0224278 A1 * 8/2015 Addington .......... A61M 16/147 128/200.21

* cited by examiner

NEBULIZER TUBING WITH A PORT TO MINIMIZE MEDICAMENT LOSS

BACKGROUND

Many patients with acute or chronic lung disease, such as asthma, emphysema, bronchitis, or pneumonia use medication delivered in an aerosol form via a nebulizer. Most nebulizers deliver medication continuously throughout a patient's respiratory cycle: inhalation and exhalation. Therefore, while the patient is exhaling, medication is lost into the atmosphere.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention. The foregoing paragraph has been provided by way of general introduction, and is not intended to limit the scope of the following claims. The described embodiments, together with further advantages, will be best understood by reference to the following detailed description taken in conjunction with the accompanying drawings.

SUMMARY

The present disclosure relates to a nebulizer tubing and valve adaptor comprising an inlet configured to be connected to a gas source and an outlet configured to be connected to a nebulizer. The nebulizer tubing comprises a port configured to be covered during inhalation to allow airflow from the gas source to the nebulizer and uncovered during exhalation to stop the airflow from the gas source to the nebulizer by allowing gas to escape from the nebulizer tubing. The airflow activates a nebulization process.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
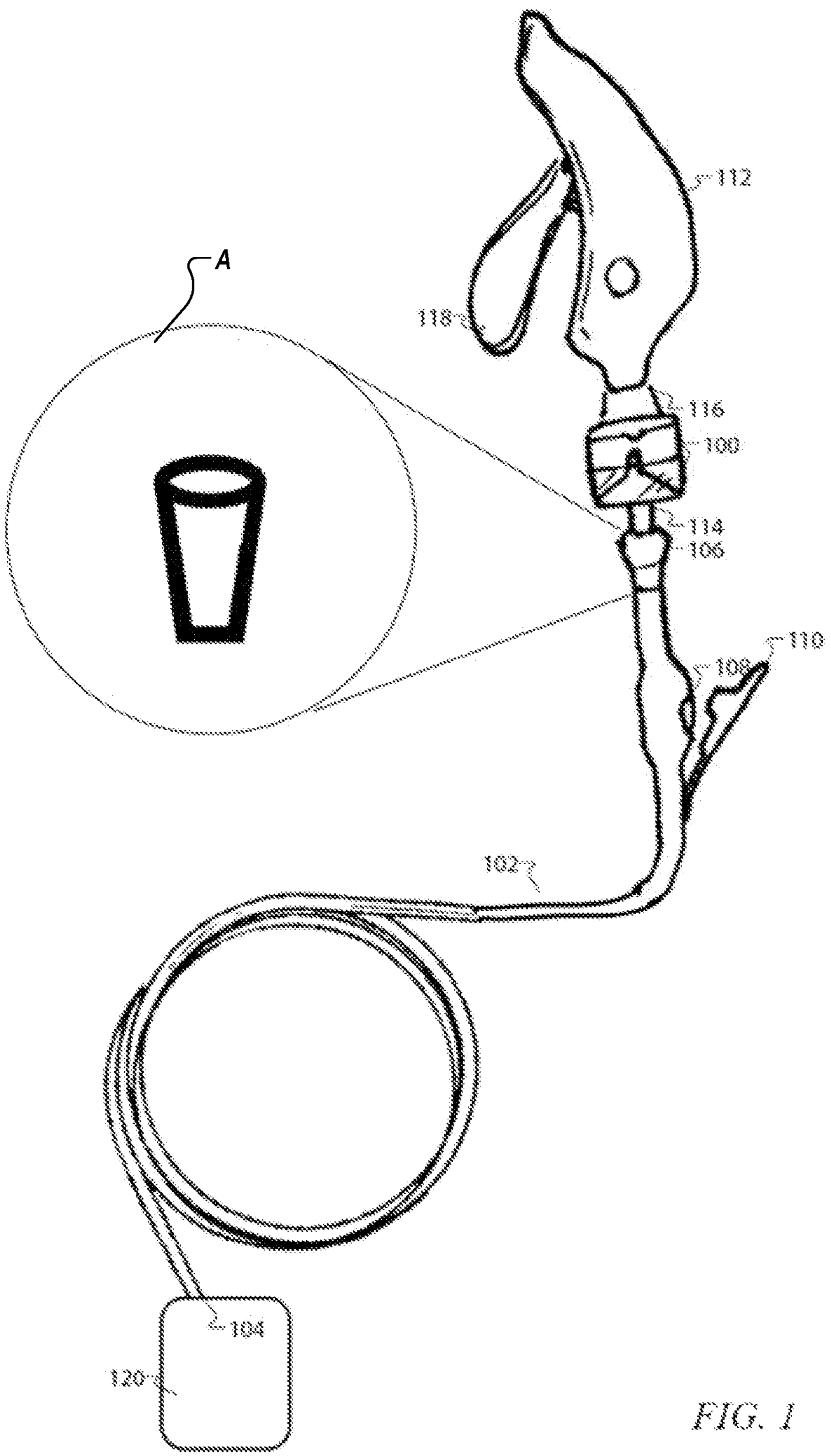
FIG. 1 is a schematic that shows a nebulizer system according to one example.

Referring now to the drawings, wherein like reference numerals designate identical or corresponding parts throughout several views, the following description relates to a nebulizer tubing and a nebulizer. The nebulizer having the nebulizer tubing described herein may be finger controlled by a patient.

Conventional small volume nebulizers (e.g., inhaler systems) are designed to provide aerosolized medication for a period of time (e.g., 15-30 minutes). Nebulizers are used for the treatment of cystic fibrosis, asthma, COPD (Chronic Obstructive Pulmonary Disease), and other respiratory diseases. Nebulizers use oxygen or compressed air to break up medical solutions and suspensions into small aerosol droplets that can be inhaled by the patient.

A nebulizer with an actuation hole located on the stem of the nebulizer itself is described in U.S. Pat. No. 4,657,007 entitled "NEBULIZER", the entire disclosure of which is incorporated herein by reference.

One problem with conventional small volume nebulizers is that the nebulizer delivers aerosol during both inhalation and exhalation, which leads to drug waste during the exhalation phase of the breathing cycle. The medication lost during treatment is a function of the patient's inspiratory to expiratory (I:E) ratio which typically ranges from 1:2 to 1:3. That is, if a patient has an I:E of 1:2, for every 1 second the patient inhales, 2 seconds are required to exhale. In addition, in patients with obstructive pulmonary disease, like asthma and COPD, the exhalation time may be more prolonged. Accordingly, if the patient inspiratory time is 1 second, and the I:E ratio is 1:3, the small-volume nebulizer that creates continuous aerosol only delivers 1 second, or ⅓, of that aerosol to the patient and the remaining 2 seconds, or ⅔, is exhaled into the atmosphere. The waste of medication increases the overall cost of healthcare. The nebulizer tubing described herein may be used with conventional small volume nebulizers. The nebulizer tubing described herein provides an inexpensive way to turn conventional small volume nebulizers into manually breath-actuated ones. That is, the nebulizer creates and delivers aerosol during the inhalation phase of the breathing cycle.

FIG. 1 is a schematic that shows a nebulizer system according to one example. The nebulizer system includes a nebulizer 100, nebulizer tubing 102, and a gas source 120. The nebulizer 100 is filled with medication and is connected to the gas source 120 (e.g., pressurized air, oxygen supply).

The nebulizer tubing 102 has an inlet 104, an outlet 106, and a port 108 located near the outlet 106. The nebulizer tubing 102 has a lower section and an upper section. The upper section is closer to the outlet 106 than to the inlet 104. The port 108 is located in the upper section of the nebulizer tubing 102 to allow easy access to the port 108 by the patient. Insert A in FIG. 0.1 shows a zoomed-in of the outlet 106.

The nebulizer 100 is connected to the gas source 120 via the inlet 104 using the nebulizer tubing 102. The nebulizer 100 may be connected to a mask 112. The port 108 may be closed fully by the patient utilizing the nebulizer 100 merely by placing a finger over port 108. The port 108 therefore provides an opening in the nebulizer tubing 102 to allow compressed air from the gas source 120 to escape from the nebulizer tubing 102 when uncovered. The port 108 may be of typical size to allow the compressed air to escape the nebulizer tubing 102 at a suitable rate as would be understood by one of ordinary skill in the art.

The nebulizer tubing 102 may be fabricated of polystyrene or other suitable plastic (e.g., C-Flex™, High density polyethylene, polypropylene, Pharmafluor®, PVC, silicone, Tygon®). The nebulizer tubing 102 may be fabricated from flexible materials (e.g., flexible plastic, Mylar™, rubber)

however; other more rigid materials may be used such as aluminum. In one aspect, the outlet 106 has a tapered diameter, where the maximum outer diameter is 12 mm, the maximum inner diameter (ID) is 8 mm and the minimum ID is 5 mm. The outlet 106 is flexible enough to strongly fit an entry port 114 of nebulizer 100. In one example, the nebulizer tubing 102 may be cylindrical having an outside diameter between 7 and 10 millimeters. To facilitate the use of the nebulizer tubing 102 with conventional nebulizers, the inlet 104 and the outlet 106 are of a shape, dimension, and/or configuration commonly used in the industry as would be understood by one of ordinary skill in the art.

The nebulizer tubing 102 may be connected to the nebulizer 100 via a friction fit allowing the nebulizer tubing 102 to easily slide off for cleaning but not disconnected due to gas pressure.

In one aspect, a hole plug 110 may be attached to the nebulizer tubing 102 adjacent to the port 108. The hole plug 110 is located in the upper section of the nebulizer tubing 102 and may be used to fully close the port 108. The hole plug 110 may be of a shape and size depending on the shape and size of the port 108. The hole plug 110 may be fabricated using the same material of the nebulizer tubing 102 or other material that ensure tight sealing of the port 108 in case a continued nebulization is needed.

Figure 5:
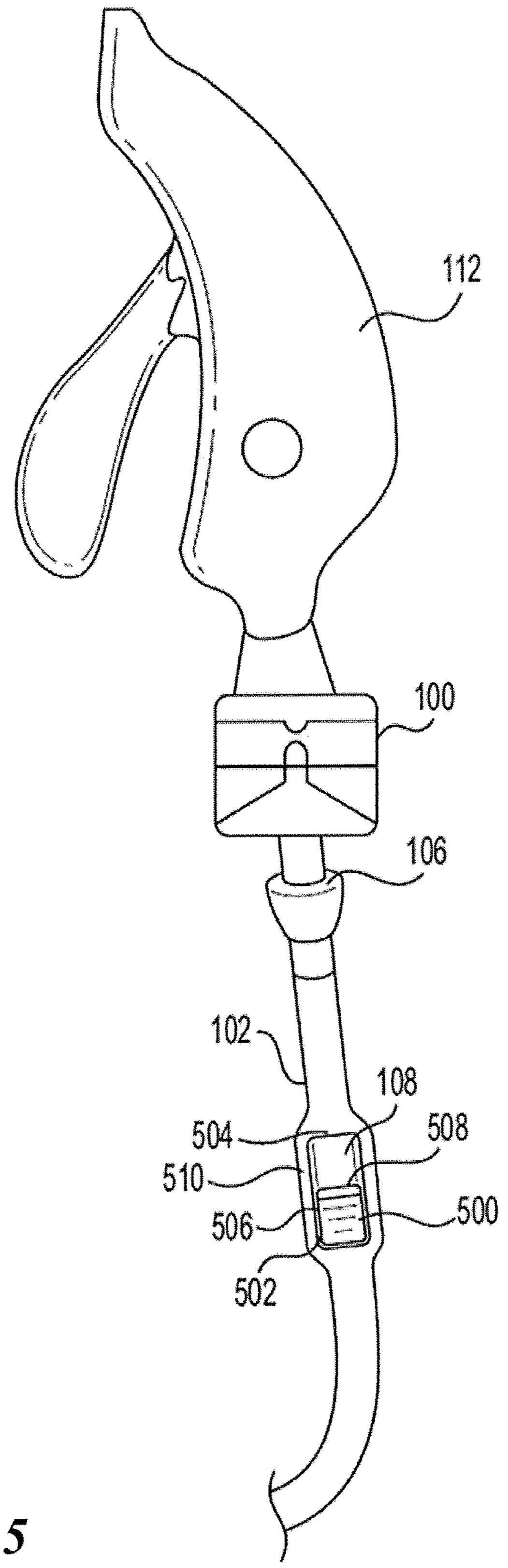
FIG. 5 is a schematic that shows the nebulizer tubing having a slidable port closure according to one example.

In other aspects, a separate cap (e.g., port cap) may be used to close port 108 when continuous delivery of medication is desired. In one example, the port 108 may have a slidable closure as shown in FIG. 5.

The nebulizer tubing 102 may be formed from a bellows type construction that permits the tube to be configured or bent at any desired angle, without affecting the gas flow, in order to accommodate the position of the patient relative to the nebulizer 100.

The nebulizer 100 is a commercial small volume nebulizer that includes a chamber having the entry port 114 and an exit port 116. The entry port 114 is configured to receive the outlet 106 of the nebulizer tubing 102. The chamber accommodates liquid medication. The nebulized material exits the chamber through the exit port 116 to a patient interface. For example, the exit port 116 may be connected to the mask 112 or to a mouthpiece (not shown) to deliver nebulized material to the lungs of the patient. The mask 112 may adhere to the patient with elastic straps 118. The nebulizer tubing 102 is configured to allow the patient to regulate the flow of nebulization by closing or opening the port 108 near the outlet 106 by finger control.

Figure 2:
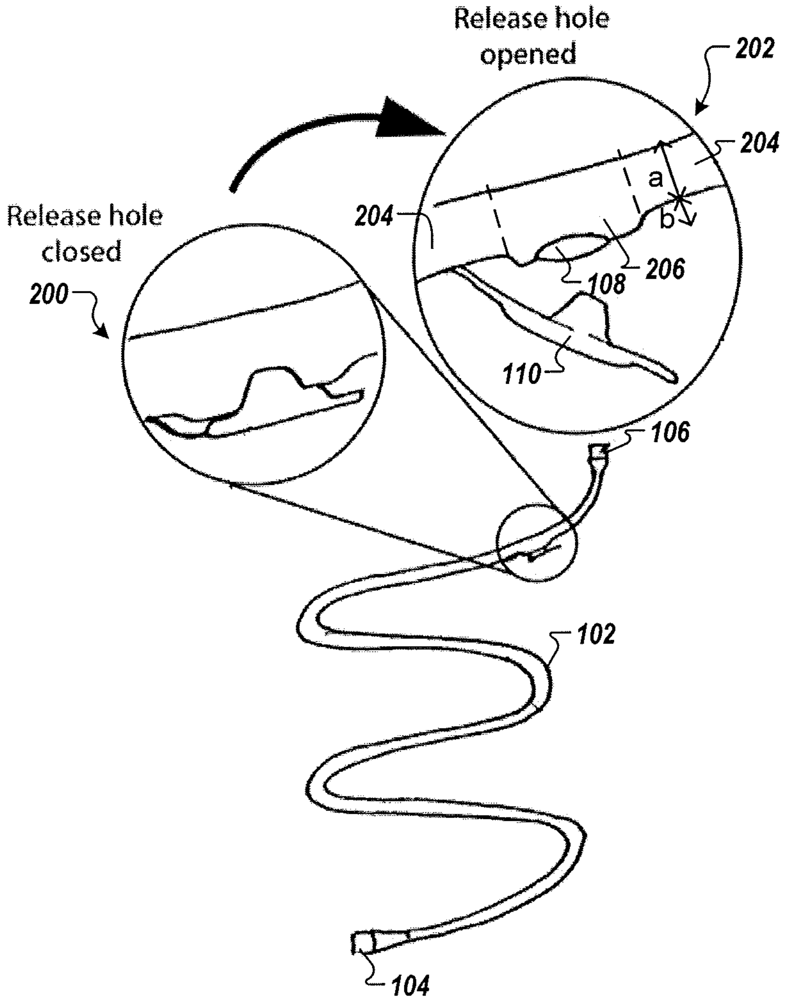
FIG. 2 is a schematic that shows a nebulizer tubing according to one example.

FIG. 2 is a schematic that shows the nebulizer tubing 102 according to one example. The nebulizer tubing 102 has two ends, the inlet 104 configured to be connected to the gas source 120 and the outlet end 106 configured to be connected to the nebulizer 100. The nebulizer tubing 102 includes a first portion 204 and a second portion 206. The first portion 204 relates to a section of the nebulizer tubing apart from the port 108. The second portion 206 relates to a portion of the nebulizer tubing 102 having the port 108 as shown by first and second dotted lines in FIG. 2. The first portion 204 has a cross-section of the nebulizer tubing 102 corresponding to a diameter distance “a” whereas the second portion 206 has a larger nebulizer tubing 102 diameter of “a+b”. Thus, the nebulizer tubing 102 in the second portion 206 extends radially farther than the nebulizer tubing in the first portion 204. The port 108 is located in the second portion 206 and thus is raised above the first portion 204 in a direction perpendicular to a length of the nebulizer tubing 102. This provides the advantage of having gas being provided from the gas source 120 to the nebulizer 100 without any restriction of air flow as the hole plug 110 (not drawn to scale) can plug the port 108 but not extend radially within the nebulizer tubing 102 as represented by diameter “a”.

Position 200 illustrates the closed port (or release hole) during continuous aerosol therapy. In position 200, the aerosol is continuously released from the nebulizer 100. Position 202 illustrates the open port during intermittent manual breath actuated aerosol therapy. In position 202, the patient controls the release of aerosol during inhalation phase of the breathing cycle. That is, the patient may cover the port 108 using a thumb while inhaling as shown in FIG. 3.

Figure 3:
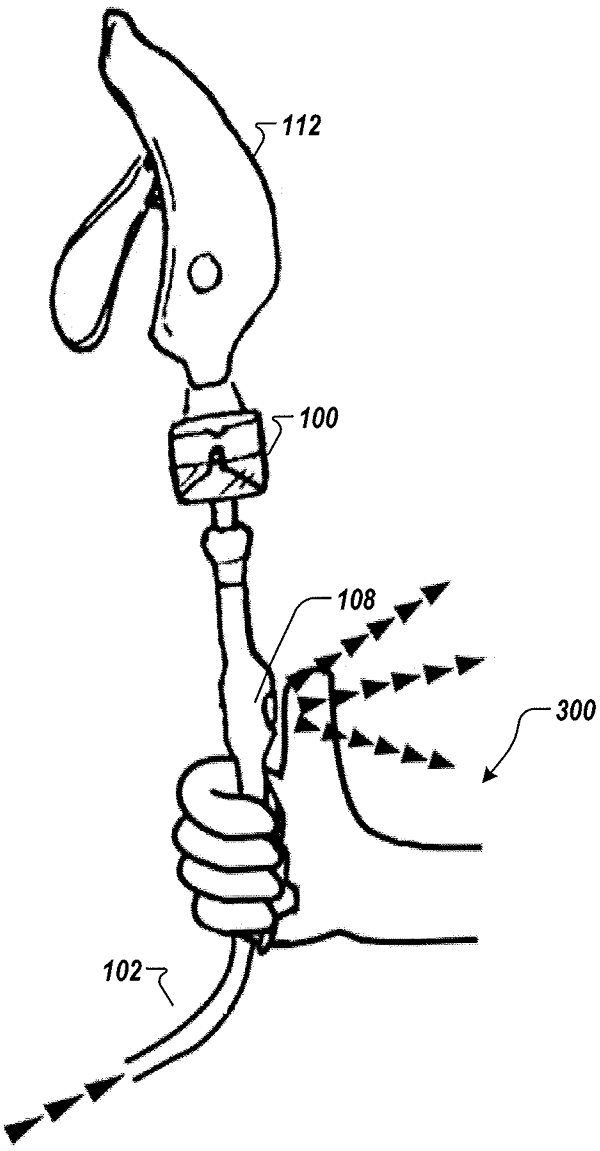
FIG. 3 is a schematic that shows the operation of the nebulizer tubing according to one example.

FIG. 3 is a schematic that shows the nebulizer tubing 102 operation according to one example. During operation, high-pressure gas is introduced to the nebulizer tubing 102 from the inlet 104 which is connected to nebulizer 100 prior to use. Gas flows at an appropriate flow rate ranging from, for example, 6 to 10 liters per minute. In a first position 300, the port 108 is uncovered, and gas escapes outside the nebulizer tubing 102 to the atmosphere before reaching the nebulizer 100. Thus, the nebulization process is not activated and aerosol is not released from the nebulizer 100. The user may uncover the port 108 during exhalation or may cover the port 108 during inhalation. Thus, during exhalations, aerosol is not released from the nebulizer 100 which minimizes the drug waste during the exhalation phase of the breathing cycle. When the user covers the port 108 during inhalation, airflow from the gas source 120 reaches the nebulizer 100 and activates the nebulization process.

Figure 4:
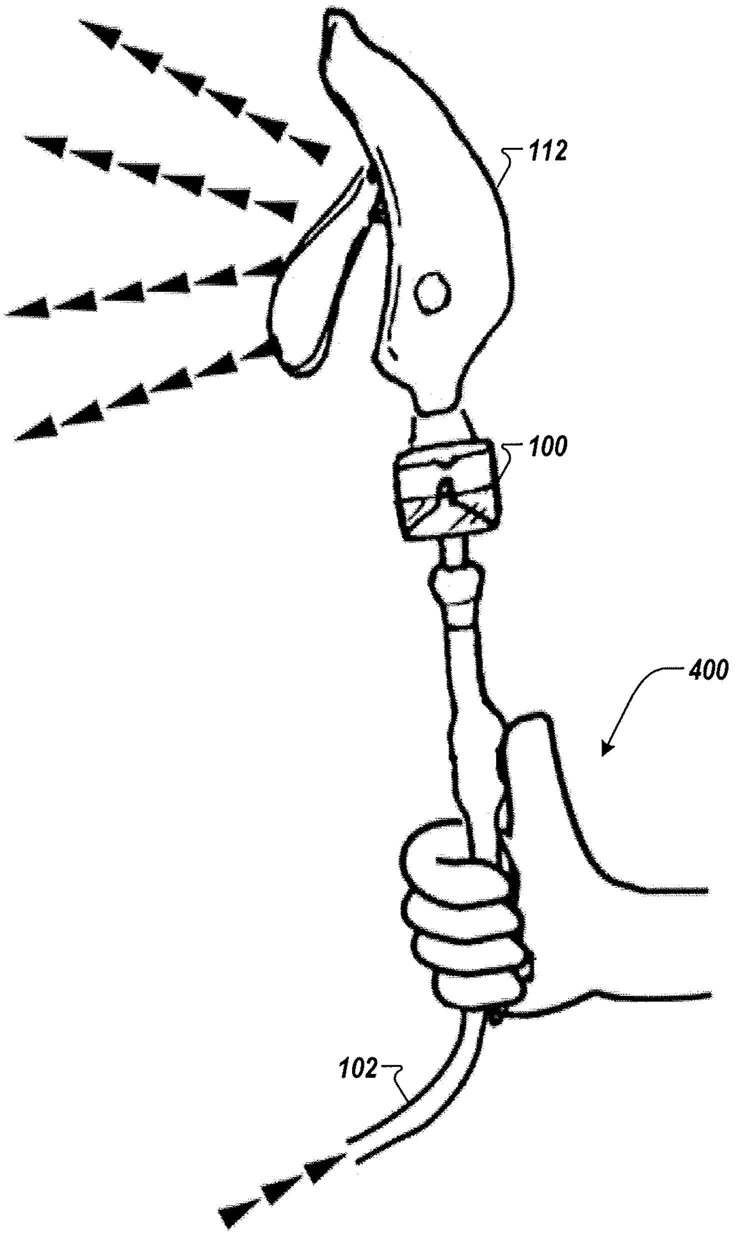
FIG. 4 is a schematic that shows the operation of the nebulizer tubing according to one example.

FIG. 4 is a schematic that shows the nebulizer tubing 102 operation according to one example. In a second position 400 with respect to the first position 300 of FIG. 3, the port 108 is closed and the gas flow is directed to the nebulizer 100 which results in the release of aerosol (i.e., liquid medicine is broken up into small aerosol particles). The patient may intermittently use a thumb or other object to cover the port 108 during inhalation which causes aerosol to be released from the nebulizer 100.

FIG. 5 is a schematic that shows the nebulizer tubing having a sliding port closure 500 according to one example. The sliding port closure 500 may include an elongated closure panel (not shown) being undermounted on the nebulizer tubing 102, a sliding cover 506, and a sliding engagement 510 (e.g., engagement tracks, post slide tracks) for permitting sliding movement between a closed position and an open position. In the closed position, the sliding cover 506 covers the port 108 and in the open position, the port 108 is uncovered by sliding back the sliding cover 506. The sliding cover 506 may include a tab 508 movable between open limit edge 502 and close limit edge 504.

The sliding engagement 510 may have undercut grooves, scalloped geometry along the longitudinal direction, or other slide tracks arrangement as would be understood by one of ordinary skill in the art.

During continuous operation, the sliding cover 506 may be fully closed. The airflow from the gas source 120 reaches the nebulizer 100 and the nebulization process is activated during both the inhalation and exhalation phase of the breathing cycle. During hand-controlled (thumb-controlled) operation or other moving methods, the sliding cover 506 may be opened as a function of the patient’s thumb size (e.g., child, adult) such that the port 108 may be fully covered by the patient’s thumb during inhalation. Thus, during the inhalation phase of the breathing cycle, the airflow from the gas source 120 reaches the nebulizer 100. The airflow activates the nebulization process which allows the release of aerosol that includes the medication. During the exhalation phase of the breathing cycle, the port is uncovered (e.g., the patient's thumb is removed, the sliding cover 506 is in open position) allowing the gas to escape from the nebulizer tubing 102 before reaching the nebulizer 100, thus the nebulization process is not activated. Thus, no aerosol is released from the nebulizer 100 during the exhalation phase of the breathing cycle. Therefore, the drug waste is minimized.

In one example, the nebulizer system may further include an airflow (breathing) sensor to detect the inhalation and exhalation phase of the breathing cycle. The airflow sensor may be a temperature sensor positioned on the nose of the patient to measure temperature. A high temperature indicates that the patient is exhaling while a low temperature indicates that the patient is inhaling. The sliding cover 506 may be controlled as a function of the output of the airflow sensor. For example, the sliding cover 506 may automatically close/open during the inhalation/exhalation phase respectively. In one aspect, the sliding cover 506 may be in a closed position when the patient starts using the nebulizer system. Then, when the airflow sensor detects the exhalation phase of the breathing cycle, the sliding cover 506 automatically closes. The sliding cover 506 may be controlled by an actuator via a microcontroller that receives the output signals of the airflow sensor. In addition, the microcontroller may determine the patient's inspiratory to expiratory (I:E) ratio based on the output of the airflow sensor, and then control the sliding cover 506 based on the patient's I:E ratio. Once the patient's I:E ratio is determined, the patient may remove the airflow sensor.

Figure 6:
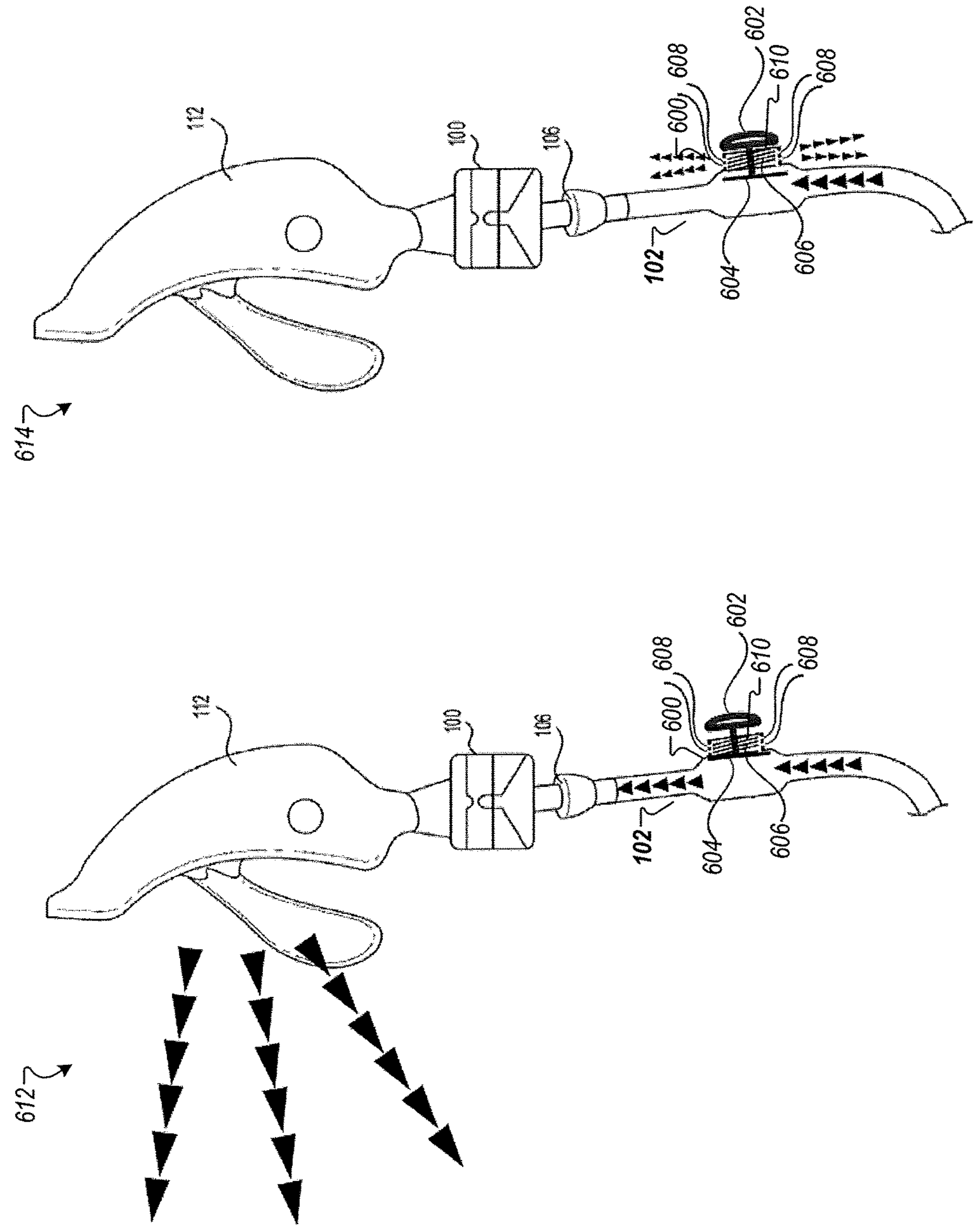
FIG. 6 is a schematic that shows the nebulizer tubing having a spring loaded actuation mechanism according to one example.

FIG. 6 is a schematic that shows the nebulizer tubing 102 having a spring loaded actuation mechanism 600 according to one example. The spring loaded actuation mechanism 600 includes an actuation button 602, a sealing disk 604, one or more springs 606, and a plurality of vent holes 608 formed all around the housing 610. The sealing disk 604 is of a size corresponding to the size of the port 108. When the actuation button 602 is pressed, the sealing disk 604 is projected to the second portion 206 of the nebulizer tubing 102 via a retracting mechanism as would be understood by one of ordinary skill in the art. For example, the retracting mechanism may include a cam or stop members attached to the actuation button 602, a lower cam (follower), and a push rod. The push rod is attached to the actuation button 602. Once the lower cam has been depressed, via the actuation button 602, to an extent sufficient to clear the stop members, the lower cam rotates under the influence of the one or more springs 606 (second position). The one or more springs 606 constantly apply an upward force. Once the actuation button 602 is released, the lower cam continues the rotational movement (third position). When the actuation button 602 is pressed again, the lower cam moves to a fourth position and then continue to rotate due to the one or more springs' 606 force to a fifth position. In another example, the spring loaded actuation mechanism 600 may include a latch mechanism to hold the sealing disk 604 in a retracted or released position.

When the actuation button 602 is in a released state, the sealing disk 604 seals port 108 and the airflow from the gas source 120 reaches the nebulizer 100, The gas pressure helps provide more sealing. The airflow activates the nebulization process which allows the release of aerosol that includes the medication. When the actuation button 602 is in a pressed state, the sealing disk 604 is pushed to the second portion 206 of the nebulizer tubing 102, thus uncovering port 108. Therefore, the gas escapes from the nebulizer tubing 102 via the plurality of vent holes 608 before reaching the nebulizer 100, thus the nebulization process is not activated. Thus, no aerosol is released from the nebulizer 100. The user may activate or press the actuation button 602 during the exhalation phase of the breathing cycle. Thus, no aerosol is released during the exhalation phase of the breathing cycle. Therefore, the drug waste is minimized. The user may release the actuation button 602 when inhaling to allow the release of aerosol that includes the medication. Position 612 illustrates the closed port when the actuation button 602 is released during continuous aerosol therapy or during the inhalation phase of the breathing cycle. In position 612, the aerosol is released from the nebulizer 100. Position 614 illustrates the actuation button in a pressed state by patient thumb during the exhalation phase of the breathing cycle. In position 614, the gas escapes from the nebulizer tubing 102, via the plurality of vent holes 608, and aerosol is not released from the nebulizer 100.

Figure 7:
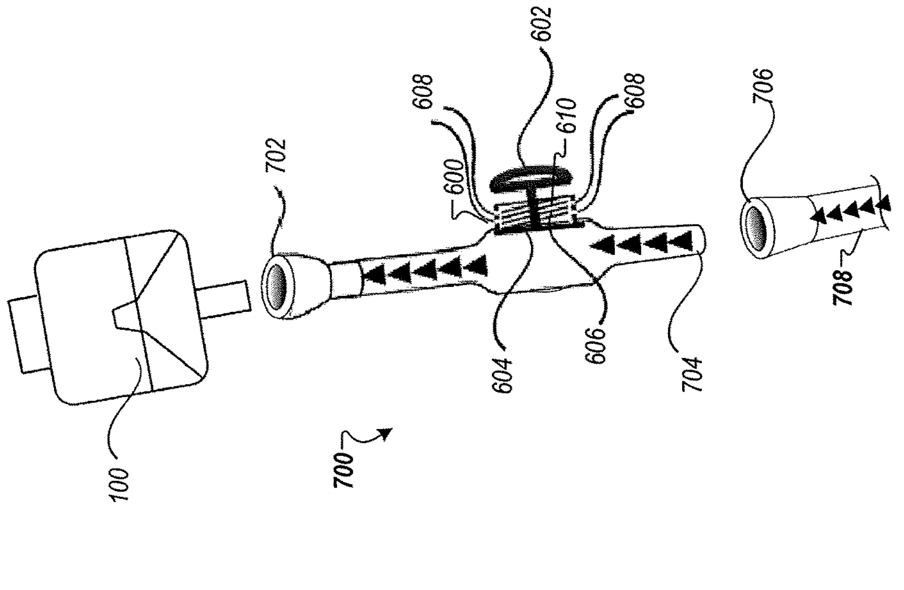
FIG. 7 is a schematic that shows an actuating valve adaptor according to one example.

FIG. 7 is a schematic that shows an actuating valve adaptor 700 according to one example. In one aspect, the actuating valve adaptor 700 may include the spring loaded actuation mechanism 600. The actuating valve adaptor 700 may include an outlet port 702 and an inlet port 704. The outlet port 702 is configured to be connected to the nebulizer 100. The inlet port 704 is configured to be connected to conventional nebulizer tubing 708 having an outlet 706. The conventional tubing 708 is connected to the gas source 120. The outlet port 702 has the same dimensions and description as the outlet 106 in FIG. 1, and the inlet port 704 of the actuating valve adaptor 700 may be of variable diameters to be connected with typical conventional nebulizer tubing. In one aspect, the actuating valve adaptor may have a tapered gradual step outer diameter ranging from 5 to 7 mm. The actuating valve adaptor can be provided individually or optionally included in a small volume nebulizer kit.

Figure 8:
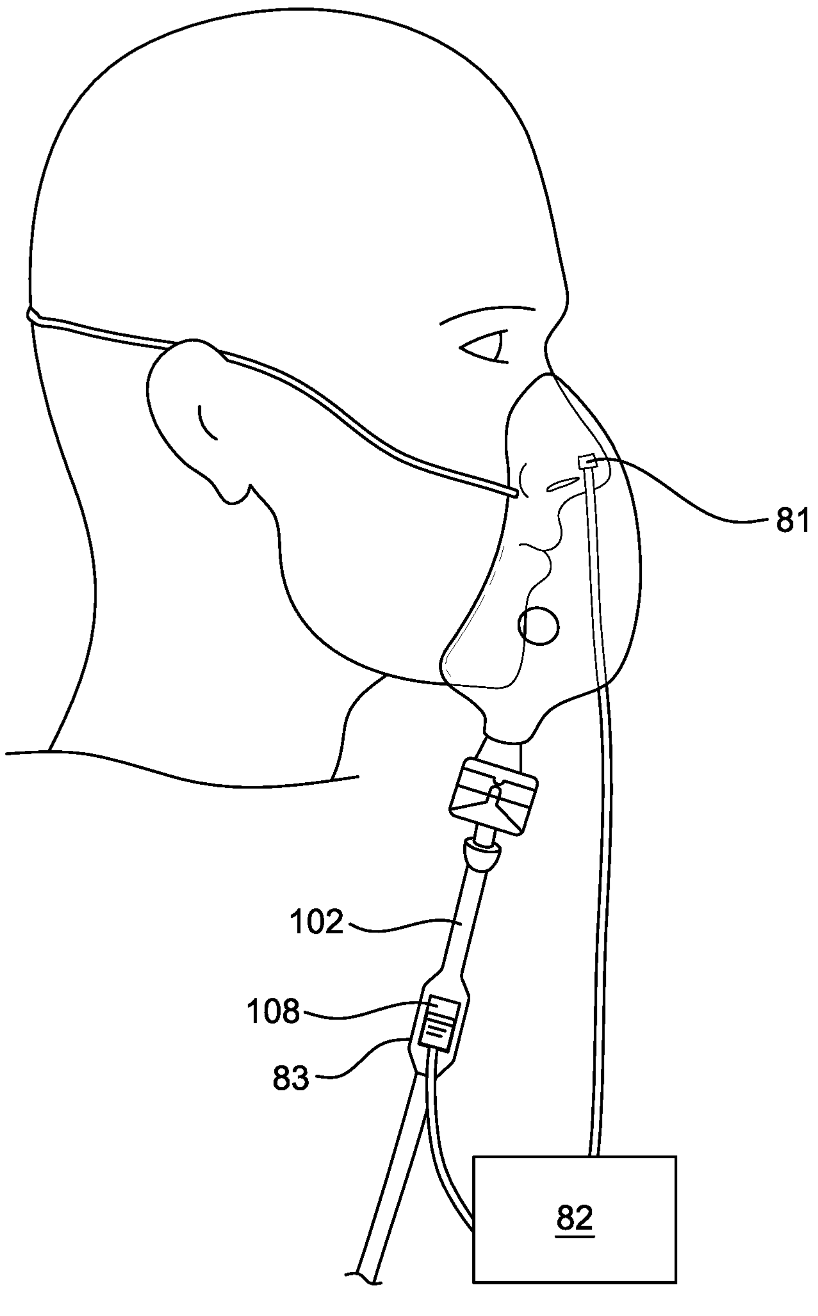
FIG. 8 is a schematic showing a nebulizer tubing according to an embodiment of the disclosure including an actuator, microcontroller and air flow sensor.

FIG. 8 shows an embodiment of the invention including an actuator, microcontroller and air flow sensor. The air flow sensor (81) includes a temperature sensor that is mounted on the nose of an individual using the nebulizing tube (102). The air flow sensor (81) is connected to a microcontroller (82) which is connected to an actuator (83) that moves a sliding port closure across the port (108).

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A nebulizer tubing consisting of:

an inlet configured to be connected to a gas source via a tube, the inlet having a tapered gradual step outer diameter;

an outlet configured to be connected to a nebulizer;

a port configured to be covered from an outer side of the nebulizer tubing during inhalation without restriction of an airflow to allow the airflow from the gas source to the nebulizer, wherein the airflow activates a nebulization process, and uncovered during exhalation to stop the airflow from the gas source to the nebulizer by allowing the airflow to escape from the nebulizer tubing, wherein the nebulizer tubing includes an upper section and a lower section, the upper section being closer to the outlet than the inlet, the port being located in the upper section, the upper section including a first portion and a second portion, the port being located within the second portion, the second portion interposing downstream and upstream lengths of the first portion, the downstream length terminating at the outlet, and the second portion having a larger constant diameter along a length of the second portion than the downstream and the upstream lengths of the first portion and thereby deliver the airflow through the second portion without restriction of the airflow; and a sliding port closure movable between a closed position and an open position, the sliding port closure covering the port in the closed position, and the port being uncovered in the open position, the sliding port closure being configured to close automatically during the inhalation and open during the exhalation, the sliding port closure being controlled by an actuator via a microcontroller that receives an output signal from an airflow sensor, wherein the airflow sensor includes a temperature sensor to identify the inhalation and the exhalation and configured to be mounted on the nose of an individual using the nebulizer.

2. The nebulizer tubing of claim 1, wherein the nebulizer tubing has a bellows configuration.

3. The nebulizer tubing of claim 1, wherein the nebulizer tubing is fabricated from a material selected from a group consisting of polypropylene, high density polyethylene, silicone, and rubber.

4. The nebulizer tubing of claim 1, wherein the nebulizer tubing is a single walled tubing.

* * * * *